United States Patent [19]

Chan et al.

[11] 4,406,770
[45] Sep. 27, 1983

[54] GAS SENSOR

[75] Inventors: Yat S. Chan, London; Anthony D. S. Tantram, Great Bookham; Bryan S. Hobbs, Chertsey; John R. Finbow, Kempston, all of England

[73] Assignee: Coal Industry (Patents) Limited, London, England

[21] Appl. No.: 344,787

[22] Filed: Feb. 1, 1982

[30] Foreign Application Priority Data

Feb. 3, 1981 [GB] United Kingdom ............... 8103258

[51] Int. Cl.³ ............................................. G01N 27/54
[52] U.S. Cl. ................................... 204/406; 204/408; 204/412; 204/415; 204/431; 204/432
[58] Field of Search ............ 204/195 P, 195 B, 195 R, 204/1 N, 1 K, 1 F, 406, 408, 412, 415, 431, 432; 128/635

[56] References Cited

U.S. PATENT DOCUMENTS

| | | | |
|---|---|---|---|
| 3,325,378 | 6/1967 | Greene et al. | 204/195 P X |
| 3,577,332 | 5/1971 | Porter et al. | 204/195 P |
| 3,755,125 | 8/1973 | Shaw et al. | 204/195 P |
| 3,776,832 | 12/1973 | Oswin et al. | 204/195 R |
| 3,824,167 | 7/1974 | Oswin et al. | 204/195 R |
| 3,886,058 | 5/1975 | Barna | 204/195 P |
| 4,126,531 | 11/1978 | Porter et al. | 204/195 P |
| 4,132,616 | 1/1979 | Tantram et al. | 204/195 P |
| 4,324,632 | 4/1982 | Tantram et al. | 204/195 P |

FOREIGN PATENT DOCUMENTS

2075197 11/1981 United Kingdom ............ 204/195 R

Primary Examiner—G. L. Kaplan
Attorney, Agent, or Firm—Stevens, Davis, Miller & Mosher

[57] ABSTRACT

A gas sensor cell assembly has planar electrodes separated by a planar hydrophilic wick which extends through the electrode into an electrolyte expansion chamber where it contacts an electrolyte. The cell is extremely compact and operates in all orientations.

17 Claims, 7 Drawing Figures

GAS SENSOR

This invention relates to electro-chemical gas sensors, more particularly to gas sensors in which the gas or vapour to be sensed is caused to react at one electrode of an electro-chemical cell which also includes a counter electrode and an intervening body of electrolyte and may also include a third reference electrode, in such a way that the current through the cell, or a characteristic potential of the cell, is a function of the concentration of the gas or vapour to be sensed.

There is an increasing demand for gas sensing instruments particularly for safety monitoring, pollution control, fire detection and flue gas analysis. There is a special demand for portable, relatively inexpensive instruments and for these to fit the application requirements, small compact, lightweight, robust, reliable and relatively inexpensive sensors are needed.

A particular problem which arises in instruments of this type is to ensure an adequate electrolyte connection between the electrodes, without which the basic operation of the cell is adversely affected. This connection needs to be stably maintained regardless of attitude changes and of the appreciable volume changes in the electrolyte that can result from changes in ambient humidity.

It is an objective of this invention to provide a small compact electro-chemical gas sensor that is simple in construction and has a high degree of integrity, reliability and freedom from the proneness to leakage and the problems mentioned above that have often been found with electro-chemical sensors.

The present invention provides an electro-chemical gas sensor in the form of an electro-chemical cell assembly comprising a first planar (sensing) electrode and a second planar (counter) electrode, and interposed therebetween and in contact therewith, a planar hydrophilic non-conducting porous separator, said separator being in contact with a hydrophilic non-conducting porous wick passing through an opening in the plane of the counter electrode and which wick extends into an electrolyte chamber partially filled with an electrolyte and contacts said electrolyte, said assembly permitting access of a gas to be sensed to the sensing electrode and providing an electrolytic connection between the sensing and counter electrodes in all orientations of the assembly.

The sensor may include a third (reference) electrode as will be described in more detail hereinafter.

Although the wick may be integral with the separator, for ease of manufacture they are conveniently two separate items of the same material. In a sensor assembly which is conveniently of cylindrical form, the wick is preferably central, and may pass through the counter electrode by means of a hole or a slit, and similarly may pass through a reference electrode. The wick arrangement of the invention ensures an adequate supply of electrolyte to the space between the electrodes quite independently of any volume change of the electrolyte (possibly caused by changes in ambient humidity and temperature) or the attitude of the cell and permits very close spacing of the electrodes with consequent reduction in size of the sensor. Thus an unusually compact sensor can be constructed.

The invention is particularly applicable to the sensing of oxidisable gases and vapours such as carbon monoxide, hydrogen sulphide, ethyl alcohol, sulphur dioxide, nitric oxide and so forth, but may also be applied to the sensing of reducible gases.

The principles will be described using the sensing of carbon monoxide as an example, but it is understood that this is simply one example of its applicability to a wide range of gases. Thus, at one electrode (anode) of the sensor carbon monoxide is electro-chemically oxidised as illustrated by the equation $$CO + H_2O = CO_2 + 2H^+ + 2e$$

At the counter electrode a reduction process must take place, for example the reduction of oxygen $$\tfrac{1}{2}O_2 + 2H^+ + 2e = H_2O$$

The overall sensor cell reaction is the sum of these two electrode reactions, namely $$CO + \tfrac{1}{2}O_2 = CO_2$$

By Faraday's law the flux of carbon monoxide reacting at the anode is proportional to the current.

If the flux of carbon monoxide to the anode is highly restricted by a suitable diffusion barrier, then substantially all the carbon monoxide reaching the anode can react, thus reducing its concentration at this point to essentially zero, so that the flux of carbon monoxide is determined by the diffusion resistance of the diffusion barrier and the concentration of carbon monoxide outside the diffusion barrier. There is therefore a direct link between the concentration of carbon monoxide and the current delivered by the sensing cell.

The diffusion barrier may take the form of a thin non-porous plastic film through which the gas to be sensed permeates by a process of solution diffusion. This, however, results in a sensor with a very high temperature co-efficient and a more preferable barrier to use is the gas phase diffusion barrier described in British Pat. No. 1,571,282 which results in a low temperature co-efficient and excellent stability. Alternatively a Knudsen diffusion barrier as described in British Pat. No. 2,049,952 may be used.

To promote the reaction of the gas to be sensed, for example carbon monoxide, at the sensing electrode, the electrode needs to contain a suitable catalyst preferably in high surface area form. Noble metals such as platinum, gold, palladium, their mixtures or alloys are commonly used sometimes with other additions to help promote the reaction. The chosen electrode material must also be a reasonable electronic conductor. Other preferred electrode materials include iridium, osmium, silver and carbon and mixtures or alloys thereof.

To allow the gas to reach the electrode catalyst without electrolyte being able to leak out of the cell through the same permeation path, a thin non-porous plastics film may be used, but a preferred form of electrode is the so-called hydrophobic electrode, such as used in fuel cell technology. In this type of electrode the finely divided active electrode is intimately mixed with fine particles of polytetrafluorethylene (PTFE) which act as a binder and which, being hydrophobic, are not wetted by aqueous electrolytes and so maintain paths for gas permeation throughout the electrode. This catalyst mix may be contained in a suitable conducting mesh, which is then finally "waterproofed" with a layer of porous PTFE on the gas side. Alternatively, the catalyst mix may be pressure bonded on to PTFE tape.

When the gas to be sensed is a reducing agent such as carbon monoxide or hydrogen sulphide which is oxidised at the sensing electrode (anode), the counter electrode (cathode) must be capable of sustaining a reduction (cathodic) process. Examples of such electrodes are lead dioxide electrodes and oxygen reduction electrodes. A third, reference electrode, may also be included to monitor or control the sensing electrode.

An acid electrolyte is normally chosen, since with alkaline electrolytes there are problems with carbon dioxide interference when monitoring gases in ambient air or in flue gases. The acid used may, for example, be sulphuric acid, phosphoric acid or perchloric acid.

Clearly all the components of the sensor that will be in contact with the electrolyte such as electrodes, current collectors and the sensor cell housing must be of materials compatible with the electrolyte. For this reason plastics such as acrylics, polyethylene, polypropylene, PTFE, ABS, have been used for constructing cell housings.

For the sensing of oxidisable gases the counter electrode is conveniently of the same type as the sensing electrode working as an oxygen reduction electrode and receiving its oxygen supply from the ambient air by radial diffusion inwardly through the porous PTFE tape from the perimeter of the tape.

When a reference electrode is provided, it may again be of similar type forming an oxygen-water couple electrode and receiving its oxygen in the same manner as described above for the counter electrode. The reference electrode may be positioned between the sensing and counter electrode or on the face of the counter electrode away from the sensing electrode. In either case the third electrode may have an opening to allow passage of the wick and an additional porous separator in contact with the wick and reference electrode to ensure an electrolyte connection. Alternatively, the third electrode may be provided on the same PTFE tape which carries the counter electrode but separate therefrom and having a separate electrical connection.

The third electrode may be used as described later to monitor or to control the potential of the sensing electrode or to control the base line of the sensor output.

Examples of construction embodying the principles of this invention are illustrated in the accompanying drawings, in which.

These drawings are not to scale, the thicknesses of some of the components, for example PTFE tape and current collectors being emphasised for the sake of clarity.

Figure 1:
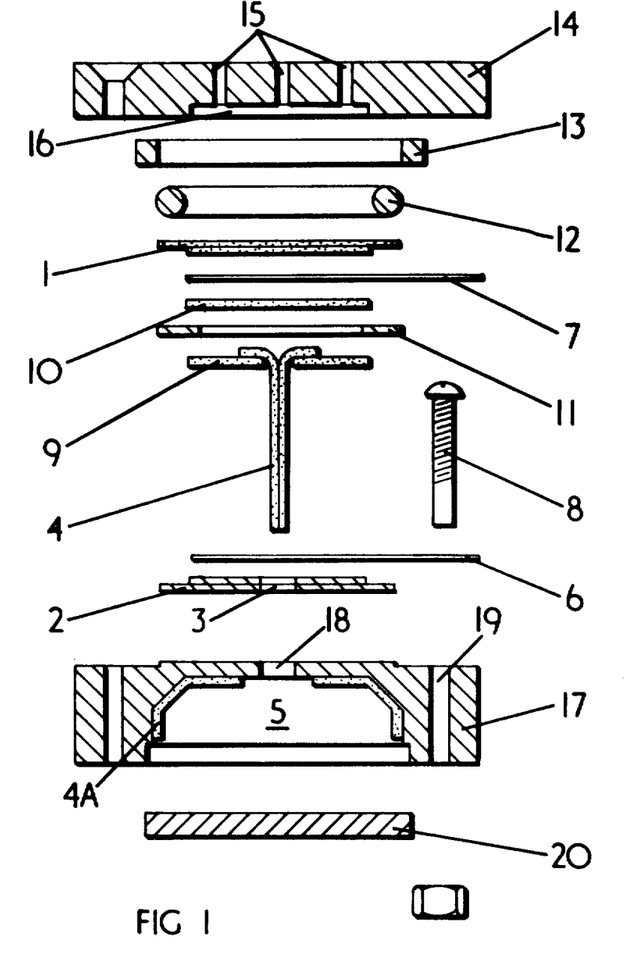
FIG. 1 is an exploded longitudinal section of a first embodiment of the invention.

Referring to FIG. 1, a sensing electrode 1 comprises porous PTFE tape to which is bonded a catalyst/PTFE mixture, the latter covering an area of smaller diameter than the tape. A counter electrode 2 is of similar construction but with a hole 3 through which a wick 4 passes to an electrolyte reservoir/expansion chamber 5.

Strip-like current collectors 7, 6 contact the sensing and counter electrodes respectively (see also FIG. 2) and lead out to terminal posts 8 (one only shown). The wick 4 extends from a separator 9 which with a further separator 10 and an annular gasket 11, which gasket may conveniently be cut from porous PTFE tape, makes up an interior sandwich between the electrodes.

Figure 1A:
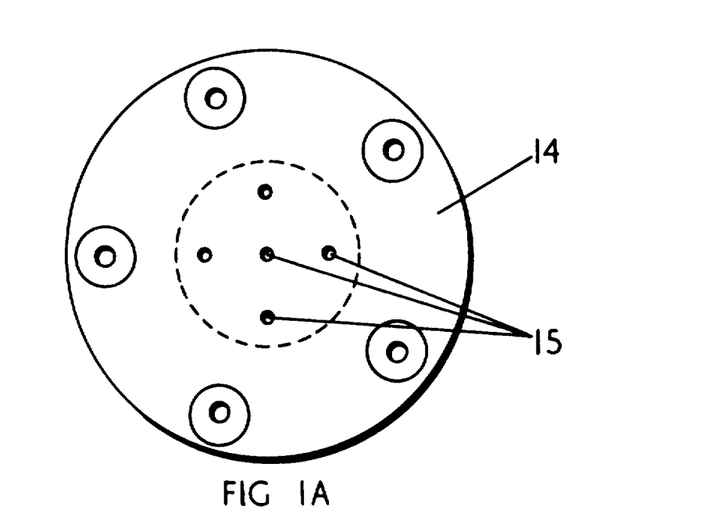
FIGS. 1A and 1B are plan views of top and bottom plates respectively of FIG. 1.
Figure 1B:
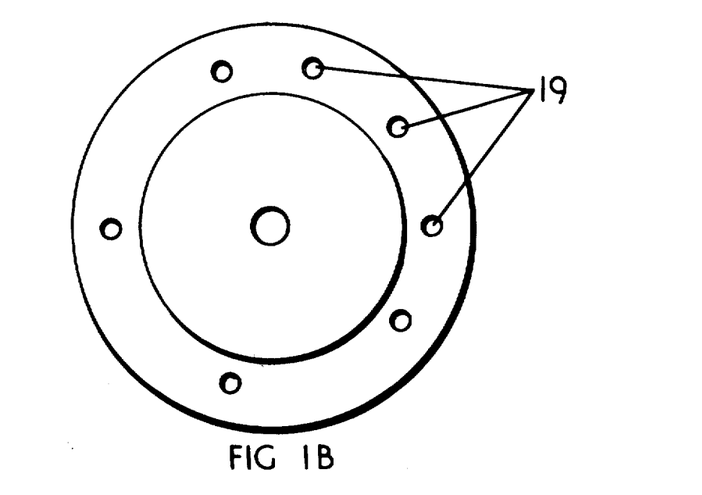

Above the sensing electrode 1 is an O-ring 12 with a rigid retaining ring 13 of smaller height than the O-ring, the underside of which has slots (not shown) to allow egress of the current collectors 6 and 7. A top plate 14 carries capillary holes 15 which form a diffusion barrier for restricting access of the gas to be detected and has a cavity 16 to allow for diffusion across the sensing electrode. A bottom plate 17 carries the electrolyte reservoir/expansion chamber 5, the wick 4 passing through a hole 18 therein, and arranged to make good contact with wick extension 4A which extends around the perimeter of chamber 5 to ensure contact with the electrolyte in all sensor attitudes. In the plan views of FIGS. 1A and 1B the holes 19 are for the terminal posts 8, the other holes being for assembly bolts.

After assembly the whole is clamped together with bolts and nuts (not shown) through the top and bottom plates 14 and 17. The nuts and bolts are tightened sufficiently to suitably compress the O-ring. The outer annular portions of the PTFE tape in the electrodes 1 and 2, not covered with catalyst, are thus brought into intimate compressive contact with the PTFE gasket 11. The PTFE moulds around the current collectors leading out of the cell from the electrodes. Sealing of very high integrity is thus achieved because of the great resistance of hydrophobic porous PTFE to aqueous penetration. The height of the ring 13 is chosen, so that the desired degree of compression is obtained by simply bolting up tight to this. O-ring compressions of between 15% and 50% have been successfully employed.

With the assembly upside down, electrolyte may now be introduced to partially fill the reservoir 5 and the cover plate 20 is sealed in position in the plate 17. The electrolyte wets up the separators 9 and 10 via the wick 4 to form the electrolyte connection between the electrodes. The amount of electrolyte is chosen to only partially fill the reservoir/expansion chamber 5 and so that volume changes resulting from gain or loss of water vapour during the operation of the sensor may be accommodated.

Figure 2:
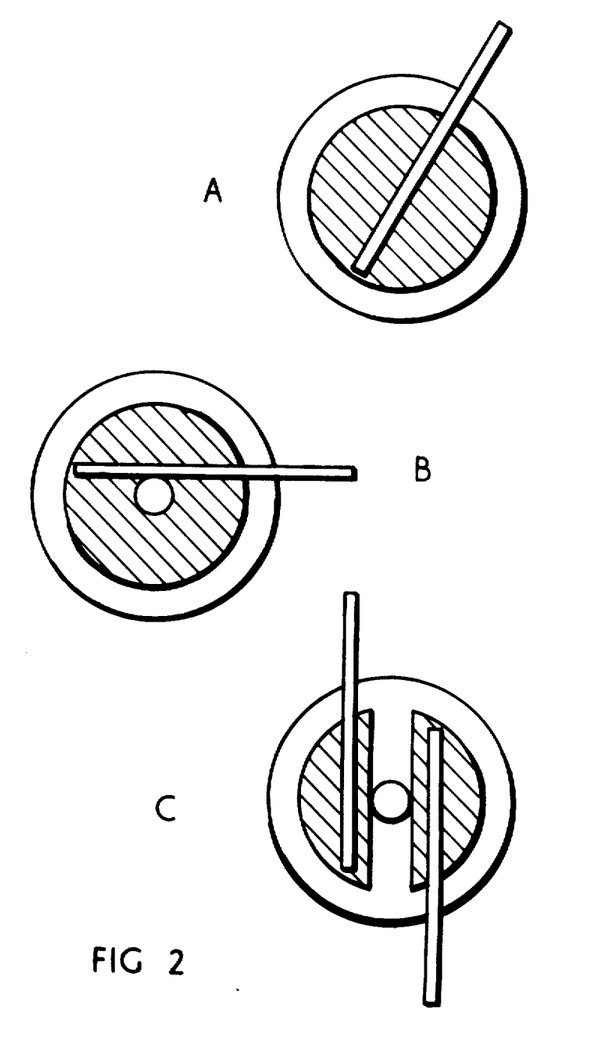
FIG. 2 is a plan view showing the arrangement of the electrodes and current collector.

In FIG. 2 the shaded areas represent the PTFE bonded catalyst areas. (a) showing the sensing electrode 1 and (b) the counter electrode 2. (c) Shows one arrangement for a three electrode system, one segment acting as counter and the other as the third, or reference, electrode. Although shown as of equal area the relative areas of counter and reference electrode may be varied as desired.

Figure 3:
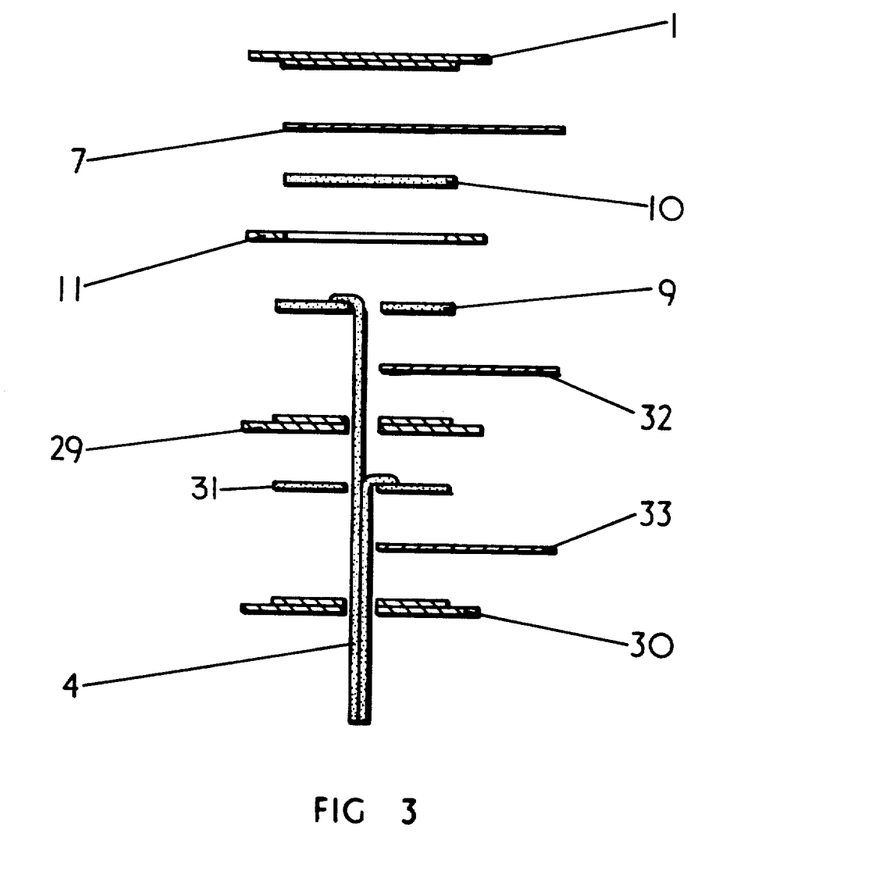
FIG. 3 is an exploded longitudinal section of part of a second embodiment of the invention.

Alternatively the third electrode may form a separate component, as illustrated in FIG. 3 which shows an exploded view of the electrodes-separators-wicked sandwich assembly, the other sensor components being as shown in FIG. 1.

Sensing electrode 1, current collector 7, separator 10, gasket 11 and separator 9 are arranged similarly as in FIG. 1. The other two electrodes 29 and 30 both have openings for the wick 4 to pass through and an additional separator 31 is placed between 29 and 30. The wick 4 is arranged to contact both the separators 10 and 31. 32 and 33 are the current collectors for electrodes 29 and 30 respectively. Electrode 29 may be used as the counter electrode with electrode 30 as the third, or reference electrode. Alternatively 30, may be used as the counter electrode with 29 as the third, or reference electrode.

Ingress of oxygen to the perimeter of the counter electrode occurs via the clearance between the current collectors 6, 7 and the slots in the O-ring retaining ring 13. To ensure good distribution around the perimeter a narrow, shallow annular channel may be cut in the bottom plate 17 with an outside diameter the same as the inside diameter of 13. From the perimeter the oxygen diffuses radially inwardly through the porous PTFE tape of the counter electrode 2 to reach the counter electrode catalyst, the PTFE tape retaining sufficient diffusibility for this purpose even when compressed by the O-ring 12. The diffusibility requirements are discussed in more detail later. If a third, oxygen reduction reference electrode is fitted, then it receives its oxygen supply by a similar route.

In an alternative arrangement the O-ring 12 is placed in between the electrodes 1 and 2 and the gasket 11 is omitted. The arrangement shown in FIG. 1 is, however, preferred since it gives more reliable sealing and avoids contact between the electrolyte and the O-ring.

Suitable materials for a number of the components were discussed earlier. The current collectors 6 and 7 must be a suitably inert conducting material and platinum ribbon is very suitable. The wick and separator material must also be inert to the electrolyte. Borosilicate glass fibre filter mat or polyester fibre mat are suitable materials.

The electrolyte concentration is preferably chosen to be approximately in equilibrium with the mean humidity that will be encountered in use to minimise overall volume changes due to loss or pick up of water. For example 10-N sulphuric acid or 50% phosphoric acid is suitable for mean relative humidities of about 65%.

Although the assembly has been described as bolted together other methods may also be used. For example glueing, ultra-sonic welding, heat welding or spring clips may be used in place of bolts. Alternatively the assembly may be enclosed in an outer metal tube and, after suitable compression of the O-ring, the ends of the metal tube crimped over to secure and maintain the assembly under pressure. In this arrangement the bolt holes through 14 and 17 are obviously unnecessary and the current collectors 6 and 7 are led out through the holes 19. For a three electrode system an additional hole will be necessary. Other variants of construction may be used without departing from the basic inventive concept.

In a further embodiment of the invention the capillaries are formed using plastic sleeves in enlarged holes 15, the sleeve material being chosen to have a larger co-efficient of thermal expansion than the material of which 14 is made. An increase in temperature will then narrow the bore of the resulting capillary as a result of differential thermal expansion and by suitable choice of materials and dimensions the intrinsically low temperature co-efficient of the gas phase diffusion barrier sensor may be further reduced to close to zero. The sensitivity of the sensor may be readily varied by varying the number and size of the capillaries to suit any required measurement range.

The sensors as so far described are suitable for operating in the diffusion mode. Alternatively, a suitable housing may be fitted to the top plate 14 to allow a gas stream to pass in a continuous flow across the sensor. When used in the diffusion mode it is clear that the ingress of the gas being monitored to the counter electrode must be much less than the ingress to the sensing electrode, so that any reaction of the gas at the counter electrode will not significantly affect the signal. At the same time, the ingress of oxygen to the oxygen reduction counter electrode must be sufficient to maintain the oxygen reduction reaction.

The situation may be analysed in the case of a carbon monoxide sensor as follows:

If the sensor signal is $= fx$ $\mu A$, where x is the concentration of carbon monoxide in ppm, and f is the sensitivity in $\mu A$ per ppm, then because the sensor is diffusion limited, the signal can be taken as a measure of gas flux to the anode (sensing electrode).

The flux of carbon monoxide to the cathode (counter electrode) needs to be very much less than that to the anode say by a factor, b, and the first condition therefore is:

$$\text{Flux of CO to cathode} \leq fx/b$$

The flux of oxygen to the cathode will be proportionately larger by the ratio of concentrations, assuming that the diffusion constants are the same for oxygen and carbon monoxide. An extra factor of 2 must also be included since units of current are being used as a measure of flux and one mole of oxygen is electro-chemically equivalent to 2 mols of carbon monoxide.

$$\text{So flux of oxygen to cathode} = \frac{fx.2}{b} \cdot \frac{2.1 \; 10^5}{x}$$

from ambient air with 21% ($2.1 \times 10^5$ ppm) oxygen.

The second condition is that this flux should be more than adequate to sustain the sensor current (fx), say by a factor a. This can therefore be written $$\frac{fx}{b} \cdot \frac{4.2 \times 10^5}{x} \geq a fx \text{ or } x \leq \frac{4.2 \times 10^5}{ab}$$

For carbon monoxide interference at the cathode to be insignificant the value of b needs to be of the order of 50 to 100. In the limit there will be an insufficient supply of oxygen when a equals 1, so the limits of carbon monoxide concentration will be 8,400 ppm for b=50 and 4,200 ppm for b=100. It can be seen that there is ample leeway for most monitoring applications where the concentrations of interest are much lower than these limits.

A sensor in accordance with the present invention is eminently suitable for meeting this requirement, it being found in practice that the fluxes fall naturally into the required range with the use of readily available porous PTFE tapes for the cathode. Additional control can be easily achieved if necessary by the choice of tape thickness, porosity, overall diameter and/or the degree of O-ring compression.

When the sensor is used in the flow mode, where the gas sample is seen only by the anode, then it is only necessary to ensure that the flux of oxygen to the cathode is sufficient for the sensor current.

Figure 4:
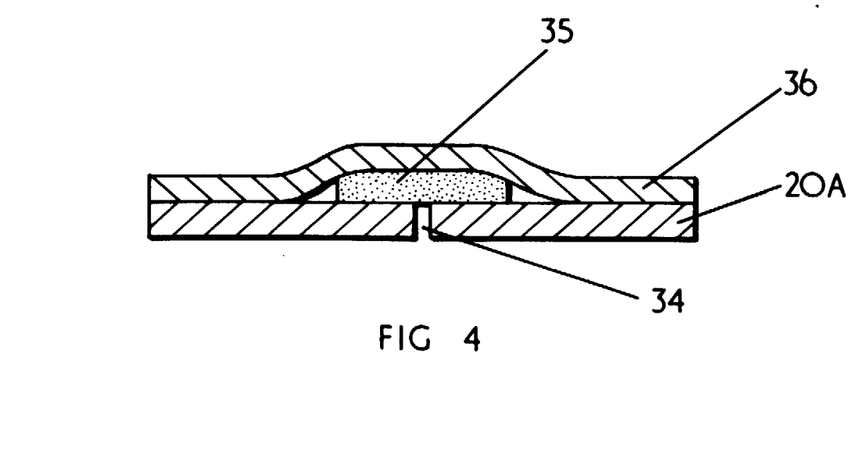
FIG. 4 is a cross-section of a part for an electrolyte chamber.

A problem that can be encountered with electrochemical gas sensors is that of internal pressure build up if the sensors are subjected to a rapid increase in temperature, which may be sufficient to force electrolyte through the seals. If there is no venting or pressure relief mechanism then the pressure of the internal gas will increase in proportion to the absolute temperature. Attempts have been made to alleviate this problem by elaborate means including the provision of flexible diaphragms which distort to accommodate the pressure changes. A novel solution to this problem takes the form of a gas vent. The principle may be readily understood by reference to FIG. 4. A cover plate 20A is used to close off electrolyte reservoir 5 of FIG. 1 (equivalent to 20 in FIG. 1, but modified in the following manner). A narrow (capillary) hole 34 passes through the cover plate. A gas permeable spacer 35 is held over the hole by a layer of porous PTFE tape 36 which is glued around the perimeter of plate 20A. After the sensor is charged with electrolyte as previously described this cover plate assembly is sealed into plate 17 as previously described for cover plate 20. The porous PTFE will allow the passage of gas but not electrolyte. Internal gas expanding as the sensor warms up can now vent through the porous PTFE 36 and the capillary hole 34. A narrow capillary hole will present a severe restriction to diffusion, but very much less restriction to bulk flow. For a sensor operating in the diffusion mode, where the atmosphere under test completely surrounds the sensor the size of the capillary hole may be readily chosen so that the rate of diffusion of the gas to be detected through the hole and subsequently via the electrolyte expansion chamber to the electrodes is slow enough to have a negligible effect on the signal but still allow for more than adequate venting. The chosen size will be dependent on the internal gas volume in the sensor, the maximum heating rate, the sensitivity of the sensor and the thickness of the plate 20A and may be readily selected by trial and error. As a guide we have found that with a 1 mm thick plate, hole sizes in the range 0.05 mm to 0.5 mm diameter have been suitable. For a 2 mm thick plate these sizes would be increased by a factor of $\sqrt{2}$ to produce a pro-rata effect. While the vent is conveniently provided in the cover plate as described it will be understood that it could be fitted elsewhere in the electrolyte reservoir expansion chamber. The vent may be applied to sensors other than those embodying the main principles of this invention.

Many sensors according to the present invention have been made and tested. The majority of these have been approximately 40 mm outside diameter and 15 mm thick, illustrating the small size and compactness made possible. They have shown an excellent record as regards orientation stability, freedom from leakage, low temperature co-efficient and signal stability over long periods of time in tests having extended over seventeen months.

When comprising only two electrodes, the cell may be operated with a simple load resistor connected between the anode and cathode and the voltage generated across this by the signal current suitably amplified. Alternatively a current follower or current-voltage converter type of circuit may be used. The provision of a third electrode may be used for conventional potentiostatic control in which the sensing electrode is held at a fixed potential independent of the concentration of the gas to be detected. It may also be used for either of the two methods of operating which will now be described.

A problem encountered with simple two electrode sensors employing an air reduction cathode when operating in pure air is that of a residual base line consequent on differences in oxygen reduction activity between the anode and cathode. According to a feature of the invention, such residual base lines are biased out by the inclusion of a third electrode in the system and by passing a constant galvanostatic current between this third electrode and the counter electrode, which is normally the cathode. The necessary value of this galvanostatic current required to offset the base line can readily be selected with any particular sensor by trial and error. For preference the cathode is selected to have a higher oxygen reduction activity than the anode, which will show up as a higher open circuit potential in pure air and in this case a positive base line (anodic at the anode) will result. In such a case the galvanostatic current necessary to reduce or eliminate the base line will be a cathodic current to the cathode from the third electrode. As well as the benefit of a reduced base line it is found that a number of other benefits ensue, notably a much sharper response and greater stability during extended exposures of the sensor to test gases. The galvanostatic current and its generating circuitry are quite independent of the sensor signal and its circuitry.

Figure 5:
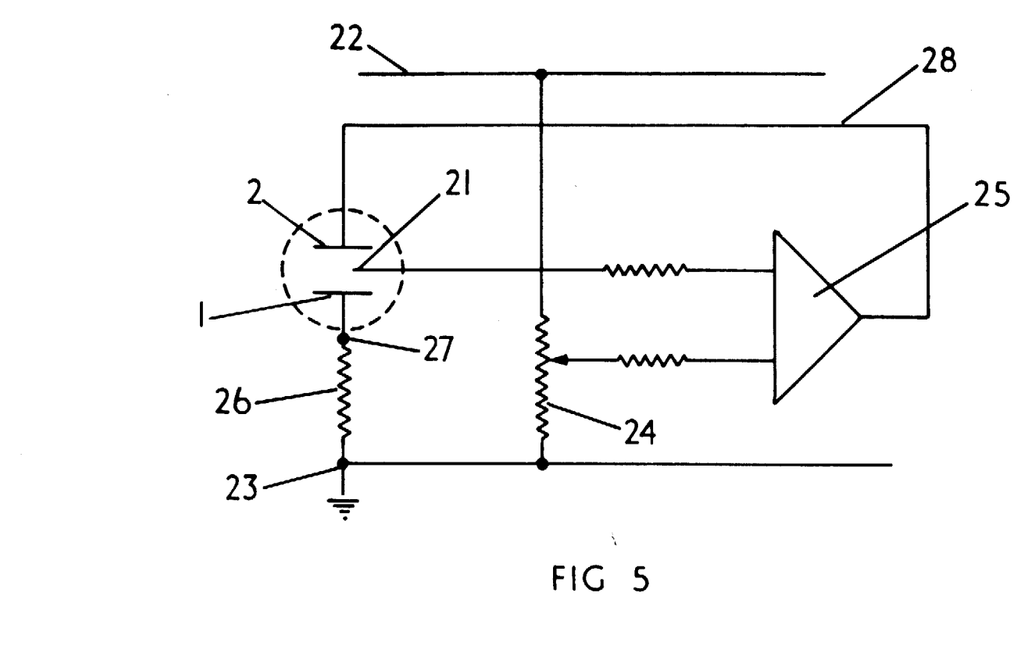
FIG. 5 is a diagram of a circuit for a sensor according to the invention.

According to a further feature of the invention, the three electrode embodiment of the sensor is part of an electronic circuit such as that shown in FIG. 5 which is so designed that the potential of the sensing electrode, e.g. the anode when sensing an oxidisable gas, varies with the concentration of the gas being monitored and the said change in anode potential may then by used as a measure of the concentration of the gas being sensed In FIG. 5 the sensing cell is shown within the dotted circle, containing the anode 1, the cathode 2 and the reference electrode 21. A reference voltage rail 22 may be supplied by electronic means or by a suitable battery such as a mercury-zinc cell. A selected voltage to apply between the reference electrode 21 and the point 23 may be achieved by the variable resistance 24. The operational amplifier 25 will then hold this voltage constant. The value of this voltage should be chosen so that undesirable side reactions in the sensing cell are minimised and will normally be chosen so that the anode is in the region of its rest potential in pure air.

If the anode is now exposed to an atmosphere containing a reducing gas to be monitored e.g. carbon monoxide, the potential of the anode will change and a current will be generated as described earlier. It can easily be seen that the change in anode potential $\Delta V$ will be given by $\Delta V = iR$ where i is the current flowing through the sensor between anode and cathode and R is the value of the load resistor 26. The change in anode potential will therefore be a function of the concentration of carbon monoxide and this signal $\Delta V$ may be taken off from points 23, 27 and if necessary amplified for display or other purposes.

It is found that this method of operation, with a load resistor and the anode potential varying as a function of the concentration of the gas being sensed has significant practical advantages compared to a known method of potentiostatic operation where the sensing electrode is held at a fixed potential in that circuit noise is very significantly reduced.

The following are some examples of sensor in accordance with the invention:

EXAMPLE I

A sensor was constructed according to FIG. 1 in which the housing components 13, 14 and 17 were of acrylic plastic; the anode was a mixture of platinum black and PTFE particles pressure bonded to porous PTFE tape 0.1 mm thick of porosity about 25% manufactured by Dodge Industries; the cathode was of similar construction but with a 3 mm diameter hole through its middle. The separator and wick were of Whatman GF/C glass fibre paper. The current collectors were of platinum ribbon. The electrolyte was 10 N sulphuric acid, the reservoir of 3 cm³ being approximately one third filled. Five capillaries in the top plate were formed by inserts of silicone rubber tubing of wall thickness 1.5 mm and giving capillary dimensions of 1 mm inside diameter and length 4 mm. This sensor had a sensitivity to carbon monoxide of 0.11 μA/ppm, and a temperature co-efficient of less than 0.05% of signal per °C. The sensor performed well without leaking in a variety of attitudes, and for many months.

EXAMPLE II

A sensor was constructed as in Example I but with only a single central control capillary of similar construction and dimensions. This sensor had a sensitivity to carbon monoxide of 0.022 μA/ppm over the range 0–1000 ppm.

EXAMPLE III

A sensor was constructed as in Example I, but using finely divided gold as the anode catalyst in place of platinum black, a mixture of platinum black and finely divided gold as the cathode catalyst, and 50% phosphoric acid in place of 10 N sulphuric acid. When tested with mixtures of hydrogen sulphide and air, the sensor showed a sensitivity of 0.39 μA/ppm to hydrogen sulphide. The sensor was reliable, with only small variations in output with temperature changes, and demonstrated integrity with freedom from leakage.

EXAMPLE IV

A three electrode sensor was constructed as illustrated in FIG. 3. All the electrodes were comprised of platinum black and PTFE particles bonded to porous PTFE tape as in Example I. The separators and electrolyte were as described in Example I. A single capillary was formed in the acrylic top plate by an insert of a silicone rubber tube of wall thickness 3 mm giving capillary dimensions of 0.875 mm bore and length 2.5 mm.

The sensor was tested using the circuit shown in FIG. 5, with electrode 29 (FIG. 3) acting as counter electrode (equivalent to 2 in FIG. 5) and electrode 30 (FIG. 3) as reference electrode (equivalent to 21 in FIG. 5). The load resistor 26 was 100 ohms. The potential between 21 and 23 was set at zero. The signal sensitivity taken across the load resistor 26 between points 27 and 23 was 3 μV per ppm of carbon monoxide. Tests with concentrations of up to 4000 ppm of carbon monoxide in air or nitrogen showed linear response and stable signals. Over the range 10° C. to 30° C. the signal varied no more than ±1.5% of its mean value.

We claim:

1. A planar electrochemical cell gas sensor comprising
    a first planar (sensing) electrode,
    a first plastics housing part having a diffusion barrier capable of permitting a gaseous atmosphere to be sensed to diffuse to contact said first planar (sensing) electrode,
    a second plastics housing part having an electrolyte chamber formed therein,
    a second planar (counter) electrode carried on a planar support, said support having a hole or slit therein,
    a planar hydrophilic non-conducting porous separator interposed between said first and second electrodes and in contact therewith, and
    a hydrophilic non-conducting porous wick in contact with said separator, said wick passing through said opening in said counter electrode and said hole or slit in said planar support and extending into said electrolyte chamber,
    said electrolyte chamber being partially filled with an electrolyte that contacts said wick and provides an electrolytic connection between the sensing and counter electrodes in all orientations of the sensor.

2. The sensor of claim 1 further comprising a capillary gas vent connecting said electrolyte chamber and the ambient atmosphere, said vent being closed on the electrolyte side thereof by a hydrophobic porous membrane capable of permitting diffusion of gas to accomodate changes in pressure but preventing the passage of electrolyte.

3. A sensor as claimed in claim 1, additionally comprising a third planar (reference) electrode.

4. A sensor as claimed in claim 3, wherein the reference electrode is in substantially the same plane as the counter electrode.

5. A sensor as claimed in claim 4, wherein the reference electrode and the counter electrode are carried on a common planar support but are electronically isolated from each other.

6. A sensor as claimed in claim 3, wherein the reference electrode is in a different plane to that of the counter electrode and is separated therefrom by a further planar hydrophilic non-conducting porous separator which is in contact with the wick, the wick passing through an opening in the plane of the further separator.

7. A sensor as claimed in claim 3, wherein the reference electrode is an oxygen-water couple electrode receiving its oxygen from ambient air.

8. A sensor as claimed in claim 7, wherein one or both of the counter electrode and reference electrode are carried on a hydrophobic porous support which extends to the surface of the assembly and permits oxygen to diffuse to the electrode.

9. A sensor as claimed in claim 3, additionally comprising means for maintaining a current between the sensing electrode and the reference electrode and means for adjusting the current in order to adjust the base line of the sensor.

10. A sensor as claimed in claim 3, comprising a resistor, having a first side connected to the sensing electrode and means to control and maintain a constant potential between the second side of the resistor and the reference electrode, whereby a signal equal to the change in potential of the sensing electrode on exposure to the gas to be detected and giving a measure of its concentration is developed across said resistor.

11. A sensor as claimed in claim 1, wherein one or more of the electrodes comprises a catalyst mixed with PTFE particles bonded to a porous unsintered PTFE tape planar support.

12. A sensor as claimed in claim 11, wherein one or more of the electrodes is a catalyst selected from platinum, iridium, ruthenium, osmium, palladium, gold, silver, carbon and mixtures or alloys thereof.

13. A sensor as claimed in claim 1, wherein the sensing electrode is an anode for the detection and measurement of oxidisable gases.

14. A sensor as claimed in claim 13, wherein the counter electrode is an oxygen reduction cathode receiving its oxygen from ambient air.

15. A sensor as claimed in claim 1, wherein the sensing electrode is a cathode for the detection and measurement of reducible gases.

16. A sensor as claimed in claim 1, wherein the diffusion barrier is selected from capillary, porous membrane, and non-porous plastics film.

17. A sensor as claimed in claim 16, wherein a capillary is used which is formed by a capillary insert in the sensor assembly and the material of the insert has a higher coefficient of thermal expansion than the material into which it is inserted.

* * * * *